US006194169B1

(12) United States Patent
Kaetzel

(10) Patent No.: US 6,194,169 B1
(45) **Date of Patent: *Feb. 27, 2001**

(54) **ENHANCED EXPRESSION OF HUMAN PLATELET-DERIVED GROWTH FACTOR IN *PICHIA PASTORIS***

(75) Inventor: David M. Kaetzel, Georgetown, KY (US)

(73) Assignee: The University of Kentucky Research Foundation, Lexington, KY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/090,381

(22) Filed: Jun. 4, 1998

(51) Int. Cl.$^7$ .......................... C12N 15/09; C12N 15/63; C12N 1/16; C12N 5/10; C12P 21/02

(52) U.S. Cl. ....................... 435/69.1; 435/69.4; 435/70.1; 435/71.1; 435/254.2; 435/254.23; 435/255.1; 435/255.5; 435/252.3; 435/69.8; 435/471; 435/320.1; 435/483; 435/325; 435/360; 435/366

(58) Field of Search ................................ 435/69.1, 69.4, 435/70.1, 71.1, 254.2, 254.23, 255.1, 255.5, 252.3, 69.8, 471, 320.1, 483, 325, 360, 366

(56) References Cited

U.S. PATENT DOCUMENTS 4,801,542 * 1/1989 Murray et al. ........................ 435/70
5,324,639 * 6/1994 Brierly et al. ..................... 435/69.4

OTHER PUBLICATIONS

Cook et al, Biochem J (281), 57–65, Jan. 1992.*
Sreekrishna et al, Gene (190) 55–62, 1997.*
Buchkolz et al, Yeast Systems For The Commercial Production of Heterologous Proteins, Bio/technology, vol. 9, pp. 1067–1072, Nov. 1991.*
Romanos et al, Foreign Gene Expression in Yeast: a Review, Yeast vol. 8, pp. 423–488, 1992.*

* cited by examiner

*Primary Examiner*—Prema Mertz
*Assistant Examiner*—Fozia Hamud
(74) *Attorney, Agent, or Firm*—McDermott, Will & Emery

(57) ABSTRACT

Enhanced yields of the platelet-derived growth factor (PDGF) B-chain are obtained using the *Pichia pastoris* yeast system. Yields of both wild-type and mutant human proteins are enhanced when the yeast is transformed with a vector containing the yeast mating factor promoter fused to a sequence encoding the mature protein. The secreted wild-type protein is indistinguishable from mature 29–32 kDa protein isolated from human and Chinese hamster ovary (CHO) cells. An RKK→EEE mutant exhibited reduced association with the cell surface and accumulated in the culture medium as 29–32 kDa forms. Stable transfection of U87 astrocytoma cells with RKK→EEE mutants of either the A- or B-chain inhibited malignant growth in athymic nude mice. Despite altered receptor binding activities, each mutant retained full mitogenic activity when applied to cultured Swiss 3T3 cells. Circular dichroism spectrophotometric analysis of the RKK→EEE mutant revealed a secondary structure indistinguishable from the wild type. Yields of PDGF protein are increased many fold and in less time over previous methods.

19 Claims, No Drawings

ENHANCED EXPRESSION OF HUMAN PLATELET-DERIVED GROWTH FACTOR IN *PICHIA PASTORIS*

STATEMENT OF GOVERNMENT SUPPORT

The present invention was supported in part by funds from the National Institutes of Health (Grant DK 45518). The Government may have certain rights in this invention.

TECHNICAL FIELD

The present invention relates to methods of protein production, purification and characterization. The invention more particularly relates to the expression of platelet-derived growth factor (PDGF), especially in the yeast *Pichia pastoris.*

BACKGROUND OF THE INVENTION

Platelet-derived growth factor (PDGF) is a potent mitogen and chemoattractant that plays critical roles in embryogenesis, cell differentiation and wound repair. PDGF is a family of three disulfide-linked glycoprotein dimers of $M_r$ 29,000–32,000 that arise from stochastic assembly of the homologous subunits, A-chain and B-chain, yielding the heterodimer PDGF-AB and homodimers PDGF-AA and PDGF-BB [for a review, see ref. 1]. The A-chain is expressed as two different forms ("long" and "short") as determined by alternative splicing, with the long form containing an extended carboxyl terminus of basic amino acids that mediates association with the extracellular matrix and is encoded by exon 6 [2]. The B-chain also contains a cationic carboxyl terminus that has been implicated in the strong association of PDGF-BB with the cell surface [3]. The activity of PDGF is mediated by two PDGF receptor isotypes, α and β, which upon ligand binding associate noncovalently to form homo- and heterodimers [4,5]. The PDGF α-receptor has a high affinity for both A- and B-chains, while the β-receptor recognizes only the B-chain [6].

X-ray crystallographic analysis of recombinant human PDGF-BB has revealed an antiparallel arrangement of the disulfide-linked B-chain monomers [7]. Each B-chain monomer is characterized by a so-called "cysteine knot" structure, consisting of three intrachain disulfide bonds and two antiparallel β-strands, interconnected by three loop segments (I–III). The cationic residues $Arg^{159}$, $Lys^{160}$, $Lys^{161}$ of the A-chain, which correspond to the loop III region of the B-chain, are demonstrated as being required for high affinity receptor binding and mitogenic activity [8]. Furthermore, a synthetic peptide containing loop III residues 157–163 of the B-chain exhibits PDGF antagonizing activity [9], while a mutation at residue $Lys^{161}$ of the B-chain is shown to interfere with high affinity binding to the α-receptor [10].

The present invention concerns the transformation of *Pichia pastoris* with a cDNA encoding the PDGF B chain. Others have used the *Pichia pastoris* system to express proteins. For instance, U.S. Pat. No. 5,324,639 discloses the expression of insulin-like growth factor-1 in *Pichia pastoris* cells. The recombinant protein is disclosed as being secreted into the culture medium at the level up to 100 times higher than results published in the literature using *Saccharomyces cerevisae* as the host cell. However, the reference does not suggest expressing PDGF in this system.

Cook et al., "Purification and Analysis of Proteinase-Resistant Mutants of Recombinant Platelet-Derived Growth Factor-BB Exhibiting Improved Biological Activity," *Biochem. J.* 281: 57–65 (1992) disclose the expression of recombinant platelet-derived growth factor-BB and two protease-resistant mutants thereof in *Saccharomyces cerevisiae.* The expression construct utilized sequences encoding the yeast α-factor pre-pro sequence upstream of the PDGF coding sequences to facilitate secretion. However, secretion into the culture medium was very low and most of the PDGF remained intracellular. The authors state that "a major limiting factor to PDGF-BB expression is, therefore, the secretion of PDGF-BB into the medium."

Craig et al., "Characterization of the Structure and Conformation of Platelet-Derived Growth Factor-BB (PDGF-BB) and Proteinase-Resistant Mutants of PDGF-BB Expressed in *Saccharomyces cerevisiae,*" *Biochem. J.* 281: 67–72 (1992) disclose structural studies of the recombinant PDGF-BB produced in Cook et al. (above). The authors conclude that the protease-resistant mutants have the same secondary and tertiary structures as the wild-type PDGF-BB. The structure is reported to be considerably different than that reported for authentic PDGF-BB.

Duan et al., "A Functional Soluble Extracellular Region of the Platelet-Derived Growth Factor (PDGF) β-Receptor Antagonizes PDGF-Stimulated Responses," *J. Biol. Chem.* 266: 413–418 (1991) disclose expression of the PDGFR extracellular domain in Chinese Hamster Ovary cells using an amplifiable marker to increase expression. The publication discloses that the protein was expressed in the culture medium at a level of 12 mg/L. The extracellular domain was extensively glycosylated, and bound to PDGF-BB with an affinity similar to that of the intact PDGF receptor. However, the reference does not teach or suggest expression of a PDGF protein in *Pichia pastoris.*

There remains a need to increase the efficiency of producing proteins generally, and PDGF proteins in particular. It is expected that with improved production methods the cost of these proteins can be brought down and their availability for treating a wide range of conditions can be increased. PDGF proteins are particularly implicated in as being useful in such applications as cancer therapy, wound healing, and the treatment of gastrointestinal ulcers.

SUMMARY OF THE INVENTION

The present invention is directed to a method of significantly increasing the efficiency of producing platelet-derived growth factor (PDGF) proteins, and thereby reducing their cost. The method is exemplified with human PDGF-BB, both wild-type and mutant forms. According to the principles of the present invention, wild or mutant PDGF is produced by transforming *Pichia pastoris* with a vector encoding the mature protein, maintaining the yeast under predetermined culture conditions, and isolating the protein from the supernatant. The PDGF proteins produced by this method are indistinguishable from corresponding mature PDGF proteins produced in humans or other systems.

A preferred aspect of the invention is where the PDGF protein assembles as a PDGF BB homodimer. More particularly, the PDGF BB protein is mammalian, preferably human, in origin. The PDGF protein can be wild-type or a mutant thereof.

DETAILED DESCRIPTION OF THE INVENTION

The present invention permits enhanced yields and production efficiencies of platelet-derived growth factor (PDGF) proteins. The PDGF can be in either a wild or mutant form. In particular, the invention entails producing the PDGF by transforming *Pichia pastoris* with a vector encoding the mature protein. Preferably, the vector encoding the mature protein is an expression vector, which further encodes a secretory peptide signal fused to the PDGF protein in order to facilitate secretion of the protein from the cells. The transformed cells are maintained under predetermined culture conditions for a desired length of time, and the protein is then isolated from the supematant. Whenever a signal peptide is employed, it is preferred that the signal is removed, e.g., proteolytically, either in vivo or in vitro prior to isolation of the mature protein so that a cleavage step can be avoided. As discussed herein, the PDGF proteins produced by this method are indistinguishable from corresponding mature PDGF proteins produced in humans or other systems.

In a preferred embodiment of the invention, the PDGF protein assembles as a PDGF BB homodimer. Preferably, the PDGF BB protein is mammalian, more preferably human, in origin. The PDGF protein can be wild-type or a mutant thereof. Contemplated mutants of PDGF include single amino acid substitutions, insertions and/or deletions, as well as multiple mutations. Exemplary of multiple mutations are two, three and higher substitutions of the residues occurring naturally in the wild protein.

Culture conditions effective to express PDGF in the transformed yeast are exemplified by those set forth hereinafter. A representative temperature range for maintaining the culture is 25–35° C., preferably 30° C. A representative time for conducting the culturing is 2–4 days, preferably 3 days. These and other parameters can be optimized for a particular scale preparation by the skilled practitioner.

Exemplary of the present invention is the expression of PDGF BB using a yeast secretory signal fused to the mature protein. In particular, a cDNA encoding amino acid residues 87–241 of PDGF BB was inserted in the plasmid pPIC9 (Invitrogen), which contains a nucleotide sequence encoding the secretory signal of the yeast α mating factor. The secretory signal targets the expressed protein to the secretory pathway in the endoplasmic reticulum and ultimately to the culture solution. The signal sequence is proteolytically removed prior to secretion, leaving only the mature human PDGF-BB as product.

An above-described plasmid has been stably transfected in Pichia and a Pichia clone has been employed to obtain 83 mg of mutant PDGF-BB (RKK→EEE) in 5 liters of crude culture supernatant. Analysis of the secreted product reveals correct proteolytic removal of the secretory signal and dimerization into a 29–32 kDa form, which is indistinguishable from the natural human product. This yield is to be compared with those reported elsewhere for full-length PDGF-BB (1.8 mg/5 L) and for a [$Ser^{28}$]PDGF-BB mutant (18.5 mg/5 L) expressed in *S. cerevisiae* [17]. Thus, the yield of the mutant PDGF-BB obtained according to an instant method is approximately 40 times greater than that obtained for the previous full-length native protein and approximately 4 times greater than that obtained for the previously described mutant. Additionally, the time required for growing the transformed yeast is reduced from 6 days to 3 days.

A related aspect of the present invention is a *Pichia pastoris* yeast cell, and culture thereof, wherein the *P. pastoris* is transformed with a vector capable of expressing a PDGF protein. Preferably, the vector encodes a signal peptide fused to the PDGF. Preferred PDGF proteins encoded by the vector are those described hereinabove.

The present invention will now be described with reference to certain examples which further illustrate, but do not limit it.

EXAMPLES

Example 1

Expression of Recombinant Proteins in Chinese Hamster Ovary Cells

The development of Chinese hamster ovary (CHO) cells expressing human PDGF B-chain (designated WT-RKK, for wild-type loop III residues $Arg^{160}$ $Lys^{161}$ $Lys^{162}$ or RKK) has been described previously [11]. Overlap extension PCR [12] was used to introduce a mutation converting the three cationic amino acids of loop III to glutamic acid residues (mutant RKK→EEE). The mutant B-chain cDNAs were expressed in DUX B11 cells 15 (originally described by Urlaub and Chasin [43]), a dihydrofolate reductase-deficient variant of CHO cells, under the control of the Rous sarcoma virus promoter. The fidelity of all PCR syntheses was verified by DNA sequencing using a standard dideoxynucleotide termination methodology (Sequenase™, U.S. Biochemicals). Methods for effecting stable transfection, conducting methotrexate (MTX)-induced gene amplification and screening of culture supernatants for production of PDGF B-chain have been described previously [11].

Example 2

Partial Purification of WT-RKK and Mutant RKK→EEE from CHO Cells

PDGF-BB-containing culture supernatants were collected over a 96 h period in serum-free DMEM as described elsewhere [8]. Proteins were partially purified by heparin-agarose (Sigma; St. Louis, Mo.) chromatography (2.5×5 cm), concentrated by ultrafiltration (Centriprep and Centricon 20, Amicon; Beverly, Mass.) and stored at −80° C. in the presence of 10% glycerol.

Example 3

Preparation of Wild-Type and Mutant PDGF-BB from *Pichia pastoris*

To obtain sufficient quantities of wild-type and mutant forms of PDGF B-chain for purification and analysis, cDNAs were constructed by PCR and inserted into the expression vector pPIC9 for expression in the yeast *Pichia pastoris* (Invitrogen; Carlsbad, Calif.). Specifically, truncated cDNAs corresponding to the mature human B-chain ($Ser^{82}$ to $Ala^{241}$) were obtained from C. Betsholtz, Uppsala, Sweden, amplified by PCR, and inserted in reading frame with the *Saccharomyces cerevisiae* α factor prepropeptide α factor sequence according to the manufacturer's protocol.

The primers used for PCR were obtained from Integrated DNA Technologies, Inc. (Coralville, Iowa). The 5'-end primer used provided an Avr II site followed by nucleotides encoding amino acids $Ser^{81}$ through $Ile^{88}$. The 3'-end primer contained a sequence encoding amino acids 236–241, followed by a TAG stop codon and a Not I recognition site. The actual primers used are as follows:

Primer 1: AAA CCT AGG AGC CTG GGT TCC CTG ACC ATT (SEQ ID NO: 1)

Primer 2: TAT GCG GCC GCT AGG CTC CAA GGG TCT CCT T (SEQ ID NO: 2)

The cDNAs encoding mutants RKK→SKK and RKK→SSS were synthesized using "megaprimer" PCR for site-directed mutagenesis [13]. The *Pichia pastoris* cells were transformed by formation of spheroplasts as described by the supplier.

For crude PDGF-BB preparations from *Pichia pastoris*, cultures were grown for 48 h in 1 L of buffered glycerol-complex medium (BMGY: 1% yeast extract, 2% peptone, 100 mM potassium phosphate pH 6.0, 1.34% YNB (yeast nutrient broth), $4\times10^{-5}$% biotin, 1% glycerol) at 30° C. with vigorous shaking (250 rpm). Recombinant protein expression was induced by suspension in 100 ml of BMMY (same as BMGY, with a substitution of 0.5% methanol for glycerol as carbon source) supplemented with casamino acids, followed by growth for 16 h at 30° C. in 1 L baffled flasks. Culture supernatants were obtained by centrifugation at 6088×g for 15 min at 4° C., and PDGF-BB was precipitated by addition of crystalline ammonium sulfate (60% saturation) and centrifugation (20,463×g, 60 min). Pellets were resuspended in 50 mM NaCl, 40 mM Hepes, pH 7.4 and residual ammonium sulfate removed by ultrafiltration. Proteins were stored at −80° C. in 50 mM NaCl, 40 mM Hepes, pH 7.4 containing 10% glycerol (PDGF freezing buffer).

Example 4

Radiorecentor and [$^3$H]Thymidine Incorporation Assays for PDGF-BB

Radioreceptor assays were conducted in A204 and rat mesangial cells (RMC, R52 line) as described previously [14, 8] using 20,000 cpm of [$^{125}$I]PDGF-BB (1200 Ci/mmol; Amersham, Buckinghamshire, England) as radioligand and unlabeled recombinant PDGF-BB proteins as competitor. Mitogenic activities of recombinant PDGF-BB proteins were determined by measuring [$^3$H]thymidine incorporation into cells as described [8].

Example 5

In Vitro PDGF Receptor Autophosphorylation

In vitro assays of PDGF receptor autophosphorylation were conducted essentially as described [15]. A204 and R52 cells (obtained from the American Type Culture Collection (ATCC) were grown to near confluence on 100-mm plastic dishes and maintained in low mitogenicity medium for 24 h. Cells were pre-chilled at 4° C. for 60 min and then incubated with PDGF-BB preparations for 10 min at 4° C. Cell lysates were incubated with either anti-PDGFRα or anti-PDGFRβ IgG (Santa Cruz Biotechnologies) for 60 min at 4° C., centrifuged for 10 min and incubated in fresh tubes containing protein A-agarose (Sigma) for 60 min at 4° C. Kinase assays were performed in 25 μL kinase buffer (20 mM Tris HCl, 1 mM DTT, 10 mM $MnCl_2$, pH 7.5) and 5 μCi [γ-$^{32}$P] ATP (3000 Ci/mmol) for 10 min at 30° C. Immunoprecipitates were analyzed by SDS-PAGE (6% polyacrylamide).

Example 6

Analysis of Heparin-Binding Activity by In Vitro Batch Assay

Mixtures containing 300 μL of a 50:50 slurry of heparin-agarose in 200 mM NaCl, 40 mM Hepes, pH 7.4 were incubated with 3 μg of PDGF-BB proteins for 15 min at 23° C. Supernatants were obtained by microcentrifugation and collected with a 23 G needle. Pellets were washed with 300 μL of buffer, which was combined with the first supernatant ("unbound" PDGF). Pellets were then washed twice with 150 μL of buffer containing 1 M NaCl, and supernatants were pooled (high salt wash fraction, or "bound" PDGF). PDGF-BB content of bound and unbound fractions were determined by ELISA.

Example 7

Metabolic Labeling of CHO Cells with [$^{35}$S]Cysteine and SDS-PAGE Analysis

WT-RKK, 33 nM MTX selected, and RKK→EEE cells ($5\times10^5$/35 mm dish) were pulse-labeled for 30 min with [$^{35}$S] cysteine (Amersham, 167 μCi in 0.5 mL; 401 Ci/mmol) and chased with a 100-fold molar excess of unlabeled cysteine as described [16]. One of two sets of cells was incubated for 10 min in the presence of 1 mM suramin (Sigma) to release cell surface bound-PDGF-BB. Immunoprecipitations, SDS-PAGE and autoradiography were performed as described previously [11].

Example 8

Purification of Pichia-Expressed PDGF-BB Proteins to Apparent Homogeneity.

To obtain WT-RKK for purification, the procedure described above was scaled up 4-fold. The protein was precipitated from supernatants with ammonium sulfate (60% saturation), resuspended in 40 mM Hepes pH 7.4 and applied to a column of phenyl-Sepharose (2.5×7.5 cm). PDGF-BB was eluted with 100 mL of a 50% solution of ethylene glycol in 40 mM Hepes, 150 mM NaCl, 20 mM Tris pH 7.4. The protein was then concentrated, exchanged into 40 mM Hepes pH 7.4 by ultrafiltration (Amicon) and applied to a column of Q Sepharose (2.5×4 cm; Pharmacia Fast Flow). The protein was eluted with a linear 200 mL NaCl gradient (0.05–1.5 M), concentrated and exchanged into 40 mM Hepes pH 7.4 by ultrafiltration. Protein was then applied to a 1×7 cm column of heparin-agarose (Sigma), equilibrated with 100 mM NaCl, 40 mM Hepes pH 7.4 and eluted with 600 mM NaCl. PDGF-BB was concentrated, applied to a 1×8 cm column of Sephadex G-25 (Sigma) equilibrated with 0.5 M urea, 10 mM glycine, pH 3.0, and further purified by Superose 12 FPLC (10×30 Pharmacia; Piscataway, N.J.), as described elsewhere [17].

The Pichia clone expressing RKK→EEE was grown in large-scale (14 L) under conditions optimized for high requirements of methanol and $O_2$, using a New Brunswick Microferm Fermenter. Five liters of cleared culture supernatant was obtained by Sharples centrifugation, yielding approximately 83 mg of PDGF-BB. After precipitation of protein from the culture supernatant with 80% ammonium sulfate, one-sixth of the precipitate was subjected to phenyl-Sepharose chromatography (2.5×18 cm). The protein was eluted in 300 ml of 50% ethylene glycol, which was concentrated and exchanged into 50 mM NaCl, 10 mM $Na_2HPO_4$, pH 7.4 by ultrafiltration. The protein was applied to a 5×5 column of Mono-Q at a flow rate of 1 mL/min and eluted with a linear 200 ml gradient (0.15–1 M NaCl, 10 mM $Na_2HPO_4$). It was further purified by Superose 12 FPLC (10×30) in a buffer of 150 mM NaCl, 10 mM $Na_2HPO_4$, pH 7.4 (flow rate 0.4 mL/min). PDGF-containing fractions were pooled, concentrated and stored in PDGF freezing buffer at −80° C. until further use. Protein concentrations were determined by amino acid compositional analysis.

Example 9

Circular Dichroism Spectrophotometry.

Spectra of purified RKK→EEE were recorded in 190–260 nm range using a Jasco 600 CD spectrometer and a 0.01 cm path length circular demountable cell. The protein was analyzed at a concentration of 0.20 mg/mL in 10 mM acetic acid, pH 3.2. The mean residue $M_r$ of RKK→EEE was estimated as 235, using an estimate of Mr for the PDGF-BB dimer of 26,000. Estimates of secondary structure were derived using software supplied by Jasco, which is based upon the method of Yang et al. [18].

Example 10

Stable Transfection of Human Glioblastoma (U87) Cells with PDGF Expression Vectors and Tumor Growth in Athymic Nude Mice.

Transfections and stable expression in the human glioblastoma cell line U87 were performed using a liposomal reagent (Lipofectin™) (Gibco/BRL; Gaithersburg, Md.), as described [19]. Cells were cultured in 162 $cm^2$ flasks in complete DMEM. On the day of injection, cells were removed by trypsinization, rinsed twice with Hanks balanced salt solution (HBSS, without phenol red; Gibco/BRL), and resuspended in 300 $\mu$L HBSS. Cells ($10^7$) from exponentially growing cultures of stable U87 transfectants were injected subcutaneously between the scapulae of 9-week-old athymic nude mice (Harlan Sprague-Dawley, nu/nu) using a 1 cc tuberculin syringe equipped with a 23-gauge needle. Two-dimensional measurements of tumors were obtained with vernier calipers.

RESULTS

Mutagenesis of the $Arg^{159}$ $Lys^{160}$ $Lys^{161}$ Sequence of the PDGF B-chain Disrupts the Ability to Bind PDGF α- and β-receptors and Induce Receptor Autophosphorylation.

Cationic amino acid residues located within the loop III region of the B-chain ($Arg^{159}$ $Lys^{160}$ $Lys^{161}$, or RKK) were substituted with the anionic amino acid glutamate or polar, uncharged serine residues to analyze the role of this region in B-chain function. In addition to the wild type (WT-RKK), three mutant proteins were expressed in the methylotropic yeast *Pichia pastoris* for functional and structural analyses. Two of the mutations consisted of substitutions of the $Arg^{159}$ $Lys^{160}$ $Lys^{161}$ sequence at each residue with either glutamate ($Arg^{159}$ $Lys^{160}$ $Lys^{161}$ to $Glu^{159}Glu^{160}Glu^{161}$, or RKK→EEE) or serine (RKK→SSS), while the third contained a single $Arg^{159}$ to $Ser^{159}$ substitution (RKK→SKK). Serine was selected due to its non-charged, but hydrophilic character, which was predicted to minimize structural disruption of the external loop III domain. To permit independent assessment of the role of the RKK motif for binding to PDGF α- and β-receptors, effects of these mutations were evaluated both in A204 cells, which express exclusively the α isotype [20] and R52 cells, which express the β isotype [11].

Compared to the WT-RKK protein, the RKK→EEE mutant was markedly impaired (by a factor of 400) in its ability to compete with [$^{125}$I]PDGF-BB for binding to both A204 (FIG. 1A, Table I) and R52 cells (FIG. 1B, Table I), indicating that one or more residues in the RKK sequence are involved in binding of PDGF-BB to both α- and β-receptors. In addition, the RKK→SSS mutant exhibited a significant decrease in slope and a slight decrease in affinity (factor of 3) when analyzed in R52 cells, although no effect of this mutation was seen on binding to A204 cells. This contrast reveals a subtle difference in the nature of the interaction of the RKK sequence with the two different receptor subclasses. Binding of the RKK→SKK mutant to PDGF receptors was unaffected in either A204 or R52 cells, suggesting a lack of a significant role for $Arg^{160}$ in the interaction between PDGF-BB and either receptor isotype.

To investigate whether the ability of PDGF-BB to activate PDGF receptors was similarly affected by disruption of the cationic region, the abilities of WT-RKK and RKK→EEE to induce receptor autophosphorylation in vitro were assessed in A204 and R52 cells. WT-RKK elicited dose-dependent autophosphorylation of 170 kDa PDGF receptor species in both A204 cells and R52 cells. In A204 cells, however, the RKK→EEE mutant was much less potent than wild type, with concentrations as high as 3 $\mu$g/mL required to elicit detectable α-receptor autophosphorylation, while no autophosphorylation of β-receptors was obtained in R52 cells. These observations correlate with the reduced receptor binding activity of RKK→EEE, indicating that disruption of the RKK motif with negatively charged glutamate residues also interferes with its ability to activate both α- and β-receptors.

The Receptor Binding-Defective Mutant RKK→EEE is Mitogenically Active.

Mitogenic activities of wild-type and mutant B-chain proteins expressed in *Pichia pastoris* were assessed by [$^3$H]-thymidine incorporation assay in NR6 cells, a variant of the Swiss 3T3 cell line which expresses primarily α-receptors (1). A steep dose-response curve was observed with WT-RKK with an $ED_{50}$ of 52 ng/mL (Table I). The RKK→SKK and RKK→SSS mutants exhibited slightly higher potencies than WT-RKK, while, surprisingly, the potency of the RKK→EEE mutant was identical to that of WT-RKK. To exclude the possibility of interference from potential contaminating mitogens in *Pichia pastoris* culture supernatants, WT-RKK and RKK→EEE were purified to apparent homogeneity prior to analysis and identical results were obtained. Similar results were obtained in β-receptor-expressing R52 cells. The ability of the receptor binding-defective mutant RKK→EEE to fully stimulate DNA synthesis suggests that PDGF-BB may stimulate entry of cells into S phase through a mechanism distinct from high affinity binding to PDGF receptors.

Alteration of the RKK Sequence Interferes with Binding of PDGF-BB to Heparin.

During initial attempts to purify the RKK→EEE mutant a dramatic loss in binding to heparin-agarose was noted. Because of the physiologically important role of heparin-containing proteoglycans in the association of PDGF-BB and the so-called "long" form of PDGF-AA with the extracellular matrix [20,21], binding of the loop III mutants to heparin was examined in further detail. To quantify heparin-binding activity of these proteins, an in vitro heparin-agarose binding assay was developed. Employing buffer conditions that were near-physiological with respect to pH and NaCl concentration, nearly 100% of WT-RKK bound to the matrix. However, binding of RKK→EEE and RKK→SSS were significantly impaired, with only 38% of each protein appearing in the bound fraction. The RKK→SKK mutant also exhibited decreased heparin-binding (74% bound), implicating $Arg^{160}$ in the binding interaction. Taken together, these results strongly suggest that the loop III region contributes to the heparin binding interface of the PDGF-BB molecule.

The RKK→EEE Mutant is Secreted as Non-Cell-Associated Species of 29–32 kDa.

The decreased heparin-binding activity of RKK→EEE in vitro suggested that the protein may be altered in its association with heparan sulfate proteoglycans (HS-PGs) in the extracellular matrix. PDGF-BB has been shown to associate efficiently with the cell surface [22,23], probably via interactions with HS-PGs [24, 25], and the cell surface-associated form is releasable with the heparin-like polyanion suramin. Thus, kinetics of cell surface association and secretion of PDGF-BB were analyzed by a pulse-chase approach in CHO cells expressing WT-RKK or RKK→EEE. As shown previously [22,11], WT-RKK appears on the cell surface within 1 h in a suramin-releasable form as a doublet of 34 and 35 kDa (p34/35) that peaks within 3 h and disappears by 24 h. Only trace amounts of non-cell-associated WT-RKK (p29–32) were seen by 24 h of chase. No significant change in suramin-releasable p34/35 was observed for the RKK→EEE mutant over the 24 h course of the experiment. However, a slight increase was apparent in the amount of mutant p34/35 appearing in the culture medium at 6 and 24 h of chase, suggesting an impairment in cell surface association. Moreover, a marked increase was seen in release of p29–32 into the culture supernatant at 6 and 24 h, consistent with an important role of the RKK motif in stabilizing association with the cell surface.

Analysis of RKK→EEE Mutant Structure by Circular Dichroism Spectroscopy.

To confirm that the diminished receptor binding and heparin binding activities of the RKK→EEE mutant were not a function of major alterations in secondary structure, Pichia-expressed RKK→EEE was purified to homogeneity as described above and analyzed by circular dichroism (CD) spectroscopy. Purity and molecular weights of recombinant protein preparations were assessed by SDS-PAGE under nonreducing and reducing (dimer-dissociating) conditions prior to CD analysis. In the absence of the reducing agent dithiothreitol, WT-RKK migrated as a complex of 28–30 kDa species, very similar to the species expressed in CHO cells [22], with trace amounts of a 15 kDa species observed in the preparation. The 28–30 kDa complex was converted upon reduction to a predominant 15.5 kDa monomeric form. The pattern of RKK→EEE molecular weight species observed under non-reduced and reduced conditions was nearly identical to that seen with WT-RKK, with the exception of a trace of a non-reducible 24 kDa contaminant and equal amounts of reduced p15.5 and a p14 species. The appearance of the monomeric p14 species of RKK→EEE was possibly the result of increased proteolytic cleavage, secondary to the high yeast culture density and longer collection time prior to harvest.

The CD spectrum obtained with the RKK→EEE protein was essentially identical to that reported for human PDGF-BB expressed in *Saccharomyces cerevisiae* [24]. The spectrum was characterized by a significant shoulder at 228 nm and strongly positive ellipticity at 190 nm, both of which were consistent with a high percentage of β-sheet structure in the molecule, estimated to be approximately 50%. The minimum center at 203 nm was indicative of high random coil content (43%), and the molecule contained only a small percentage of α-helical residue content (7%). These secondary structure estimates are also in close agreement with those obtained previously for PDGF-BB [24], as well as with the PDGF-BB structure derived directly by X-ray diffraction [22]. The lack of any detectable significant disruption in secondary structure for the RKK→EEE protein strongly suggests that the impairment in binding to receptors and heparin, as well as the increased secretion of the protein, were not the result of major structural perturbations in the molecule.

Loop III Mutants of the PDGF A- and B-chains Exhibit Dominant-Negative Activity.

The receptor binding-deficient RKK→EEE mutants of the PDGF A-chain [8] and B-chain remain able to dimerize, suggesting a potential for dominant-negative activity via inactivation of endogenous PDGF monomers. The human glioblastoma cell line U87 was employed for assessment of dominant-negative activity, since a PDGF autocrine loop drives its malignant growth, even in the absence of exogenous growth factors such as serum [19]. U87 cells were stably transfected with cDNAs encoding wild-type A- and B-chains, as well as their RKK→EEE mutant counterparts, as described above. When growth characteristics of transfected U87 clones were assessed in cell culture, one of the A-chain RKK→EEE expressing clones ($A^{cm}$8.1), exhibited a dependence upon exogenous growth factor (i.e., fetal bovine serum) consistent with disruption of the PDGF autocrine loop by this construct.

The effects of RKK→EEE mutant expression on malignant growth of U87 cells were also evaluated in athymic nude mice. Neomycin-resistant controls (Neo) all developed prominent tumors that were detected within approximately seven days and reached an average size of 3 $cm^3$ within 30 d. The growth of tumors from clones overexpressing either A-WT-RKK or B-WT-RKK was not significantly different from that of Neo controls. However, overexpression of either A-RKK→EEE or B-RKK→EEE almost totally curtailed tumor growth in vivo. In two of three A-RKK→EEE clones examined (8.1 and 8.4), no tumor development was observed over a 30 d time course, while only small tumors (<1 $cm^3$) could be observed by 40 d in the third clone (7.1). Similar results were obtained with the three B-RKK→EEE clones evaluated. Taken together, these results indicate dominant-negative activity of RKK→EEE mutants of the PDGF A- and B-chains, and support previous evidence [19] for a role of PDGF in mediating growth of U87 cells in vitro and in vivo.

DISCUSSION

Conversion of the RKK sequence to triglutamate (RKK→EEE) resulted in a marked loss in the ability to bind PDGF receptors and induce receptor autophosphorylation . Substitutions of the RKK sequence with the polar, uncharged amino acid serine were not as disruptive to receptor binding as glutamate substitutions, although conversion of all three residues to serine resulted in a small decrease in binding to β-receptors and a significant decrease in the slope of the β-receptor binding curve. The ability of serine to partially substitute for the RKK sequence suggests that its hydroxyl moieties can form stabilizing bonds (i.e., hydrogen bonds) with receptor. The marked inhibitory effect of glutamate residues suggests an inability of this amino acid to form such bonds, or possibly electrostatic repulsion with receptor. Consistent with this notion is the observation that substitution at $Lys^{161}$ with uncharged, non-polar alanine impairs α-receptor binding by a factor of 4–10, while substitution with negatively charged aspartate reduces binding to both α- and β-receptors by a factor of>10 [10].

Previous studies have indicated that cationic amino acids encoded by the sixth exons of the PDGF A- and B-chains play an important role in the abilities of PDGF-AA and -BB to remain associated with the cell surface and extracellular matrix via binding interactions with heparan sulfate proteoglycans (HS-PGs) [20,28]. This association is mediated by interactions with the heparin-like glycosaminoglycan (GAG) moieties of the HS-PG [20,29–31] and is considered to involve electrostatic interactions between the cationic amino acids in the PDGFs and negatively charged groups of the polysaccharide. The biological importance of this interaction is indicated by the inhibition of PDGF-induced mitogenesis with either heparin-like GAGs or cationic peptides derived from the region encoded by exon 6 of the A-chain [28,30]. The current study suggests, however, that regions other than the exon 6-encoded sequence, such as the loop III domain, contribute to heparin binding activity of the B-chain. The partial loss in heparin binding observed with the RKK→SKK mutant indicates a specific role for $Arg^{160}$, while the more marked inhibition resulting from simultaneous substitutions at all three residues (RKK→EEE and RKK→SSS) strongly suggests that one or both of the remaining residues ($Lys^{161}$ and $Lys^{162}$) also contribute to the binding interaction.

A role of the RKK sequence for mediating binding between the cell-associated 34/35 kDa species and the extracellular matrix is supported by pulse-chase analyses of CHO cells that express the RKK→EEE mutant. The accumulation of the 29–32 kDa species of RKK→EEE, and to a lesser extent, the 34/35 species in the culture supernatant suggests a lower affinity of the mutant for extracellular matrix. These data indicate that the previously characterized C-terminal retention domain of the B-chain, which remained intact in the 34/35 species of the RKK→EEE mutant, is insufficient to mediate full association of PDGF-BB with the cell surface and extracellular matrix. Taken together, the in vitro heparin binding and pulse-chase studies suggest that the heparin-binding interface of the PDGF-BB molecule is comprised of cationic amino acid residues found in both the loop III and C-terminal regions.

The lack of impairment in mitogenic activity of the receptor binding-deficient RKK→EEE mutant was unexpected, especially since the analogous RKK→EEE mutant of the A-chain is equally impaired in its receptor binding and mitogenic activities [8]. Dissociation of binding and mitogenesis is precedented, however, in studies of PDGF and other growth factors. For example, Clements et al. [36] demonstrated that substitution for $Arg^{108}$ with glutamate in the PDGF B-chain significantly impaired its ability to bind receptor (by a factor of approximately 10) and to stimulate inositol lipid turnover (by a factor of >35), but did not affect mitogenic activity. In addition, a recent study has demonstrated that FGF can induce mitogenic signaling in the presence of high concentrations of heparin that interfere with high-affinity receptor binding [37].

How can mitogenic signaling be elicited by growth factors without high affinity binding to receptors? A PDGF receptor-independent pathway for mitogenic signaling is unlikely, since many studies have demonstrated the necessity of receptor tyrosine kinases for mitogenesis induced by PDGF [38], FGF [37] and other ligands. A second possibility, that the RKK→EEE protein can fully stimulate mitogenesis through a minimal degree of receptor occupancy, also seems improbable since the $ED_{50}$ for mitogenesis of the mutant is unaltered. In a study of FGF/FGF receptor interactions [39], a model termed "transient receptor binding" is proposed in which a low affinity ligand may elicit mitogenic signaling if the on-rate of binding is significant.

Overexpression of PDGF A- and B-chains harboring the RKK→EEE mutation inhibited focus formation of U87 astrocytoma cells in culture, with the A-chain RKK→EEE mutant conferring a dependence upon exogenous serum growth factors for growth. The growth inhibitory activities of both the A-chain and B-chain RKK→EEE mutants on U87 tumors in athymic nude mice suggest that high affinity binding, mediated in part by interaction between the RKK domain and PDGF receptor, is required for maintenance of the malignant phenotype of these cells. The efficacy of these and other dominant-negative PDGF mutants [40,19,15] suggest possible avenues for gene therapy approaches to astrocytoma and other cancers for which autocrine and paracrine activities of PDGF may play a role.

The present invention has been described with reference to certain examples for purposes of clarity and understanding. It should be understood however that the invention can be practiced with modifications and/or improvements without departing from the scope of the appended claims and their equivalents.

REFERENCES

The pertinent portions of the following references are incorporated herein by reference.

1 Heldin, C.-H. (1992) *EMBO J.* 11, 4251–4259

2 Raines, E et al. (1990) in *Handbook of Experimental Pharmacology* (Sporn, M. B. and Roberts, A. B. eds.), Platelet-derived growth factor. pp. 173–261, Springer-Verlag, Berlin 3 Kelly, J. et al. (1993) *J. Cell Biol.* 121, 1153–1163

4 Yarden, Y. et al. (1986) *Nature* 323, 226–232

5 Matsui, T. et al. (1989) *Science* 243, 800–803

6 Bowen-Pope, D. et al. (1989) *J. Biol. Chem.* 264, 2502–2508

7 Oefner, C. et al. (1992) *EMBO J.* 11, 3921–3926

8 Fenstermaker, R. et al. (1993) *J. Biol. Chem.* 268, 10482–10489

9 Engstrom, U., et al. (1992) *J. Biol. Chem.* 267, 16581–16587

10 Kreysing, J. et al. (1997) *FEBS Letters* 385, 181–184

11 Kaetzel, D. et al. (1996) *Biochim. Biophys. Acta* 1298, 250–260

12 Ho, S. et al. (1989) *Gene* 77, 51–59

13 Higuchi, R. (1990) in *PCR protocols: a guide to methods and applications* (Innis, M. A., Gelfand, D. H., Sninsky, J. J. and White, T. J. eds.), pp. 177 Academic Press, San Diego 14 DiCorleto, P. et al. (1983) *Proc. Natl. Acad. Sci. USA* 80, 1919–1923

15 Vassbotn, F. et al. (1993) *Mol. Cell. Biol.* 13, 4066–4076

16 Kaetzel, D. et al. (1989) *Mol. Endocrin.* 3, 1765–1774

17 Cook, A. et al. (1992) *Biochem. J.* 281, 57–65

18 Yang, Y. et al. (1986) *Methods Enzymol.* 130, 208–269

19 Shamah, S. et al. (1993) *Mol. Cell. Biol.* 13, 7203–7212

20 LaRochelle, W. et al. (1991) *Genes & Dev.* 5, 1191–1199

21 Raines, E. et al. (1992) *J. Cell Biol.* 116, 533–543

22 Ostman, A. et al. (1992) *J. Cell Biol.* 118, 509–519

23 hyberg, J. et al. (1990) *J. Cell Sci.* 97, 219–229

24 Esko, J. D. (1991) *Curr. Opin. Cell Biol.* 3, 805–816

25 Spivak-Kroizman, T. et al. (1994) *Cell 79, 1015–1024*

26 Craig, S. et al. (1992) *Biochem. J.* 281, 67–72

27 Wiesmann, C. et al. (1997) *Cell 91, 695–704*

28 Bywater, M. et al. (1988) *Mol. Cell. Biol.* 8, 2753–2762

29 Maglione, D. et al. (1991) *Proc. Natl. Acad. Sci. USA* 88, 9267–9271

30 Fager, G., et al. (1992) *In Vitro Cell Dev. Biol.* 28A, 168–175

31 Fager, G., et al. (1992) *In Vitro Cell Dev. Biol.* 28A, 176–180

32 Khachigian, L. et al. (1992) *J. Biol. Chem.* 267, 7478–7482

33 Cardin, A. et al. (1989) *Arteriosclerosis* 9, 21–32

34 Fager, G. et al. (1995) *J. Cell. Physiol.* 163, 380–392

35 Ruoslahti, E. et al. (1991) *Cell* 64, 867–869

36 Clements, J. et al. (1991) *EMBO J.* 10, 4113–4120

37 Krufka, A. et al. (1996) *Biochemistry* 35, 11131–11141

38 Escobedo, J. et al. (1988) *J. Biol. Chem.* 263, 1482–1487

39 Nugent, M. et al. (1992) *Biochemistry* 31, 8876–8883

40 Mercola, M. et al. (1990) *Genes Dev.* 4, 2333–2341

41 Tomayko, M. et al. (1989) *Cancer Chemother. Pharmacol.* 24, 148–154

42 DeLean, A. et al. (1978) *Am. J Physiol.* 235, E97–E107

43 Urlaub, G. et al. (1980) *Proc. Natl. Acad. Sci. USA* 77: 4216–4220.

TABLE 1

Biological activity of PDGF-BB mutants

| | RRA: $IC_{50}$ (ng/ml) | | Mitogenesis |
|---|---|---|---|
| Protein | α | β | $ED_{50}$ (ng/ml) |
| WT-RKK | 9.2 | 4.0 | 52 |
| RKK → SKK | 2.3 | 2.2 | 28 |

TABLE 1-continued

| Biological activity of PDGF-BB mutants | | | |
|---|---|---|---|
| | RRA: $IC_{50}$ (ng/ml) | | Mitogenesis |
| Protein | α | β | $ED_{50}$ (ng/ml) |
| RKK → SSS | 6.5 | 13.8 | 12 |
| RKK → EEE | 4040 | 1240 | 52 |

Data were derived from radioreceptor (RRA) and mitogenesis assay data. $IC_{50}$ and $ED_{50}$ values were calculated using the four-parameter logistic equation described by the ALLFIT algorithm [42].

TABLE 2

| Secondary structure for wild-type and RKK → EEE mutant PDGF-BB obtained by circular dichroism Percentage of molecules in each | | |
|---|---|---|
| Structure (%) | PDGF-BB | RKK → EEE |
| Helix | 4.0 | 7.4 |
| Beta | 51.0 | 50.0 |
| Random | 45.0 | 42.6 |

As reported by Craig et al. (1992) for circular dichroism PDGF-BB expressed in *Saccharomyces cerevisiae*

What is claimed is:

1. A method of producing a platelet-derived growth factor PDGF BB or mutant thereof comprising:

transforming *Pichia pastoris* yeast with an expression vector encoding the PDGF BB or mutant thereof fused to a secretory signal, wherein said PDGF BB is a PDGF BB homodimer and said mutant has mitogenic activity similar to that of said PDGF BB homodimer;

maintaining the transformed yeast under culture conditions effective to express the PDGF BB or mutant as the mature protein in the culture supernatant; and isolating the protein from the supernatant.

2. The method of claim 1, wherein the PDGF is human in origin.

3. The method of claim 1, wherein the PDGF is wild-type.

4. The method of claim 1, wherein the PDGF is a mutant of wild-type.

5. The method of claim 1, wherein the PDGF BB homodimer is the human 29–32 homodimer.

6. The method of claim 1, wherein the secretory signal is the secretory signal of yeast α mating factor.

7. The method of claim 1, wherein the expression vector is pPIC9 modified to contain a nucleotide sequence encoding PDGF.

8. A culture of *Pichia pastoris* transformed with an expression vector encoding a PDGF BB protein or mutant thereof fused to a signal peptide, wherein said PDGF BB is a PDGF BB homodimer and said mutant has mitogenic activity similar to that of said PDGF BB homodimer.

9. The culture of claim 8 wherein the PDGF is human in origin.

10. The culture of claim 8, wherein the PDGF is wild-type.

11. The culture of claim 8, wherein the PDGF BB homodimer is the human 29–32 homodimer.

12. The culture of claim 8 wherein the signal peptide is the secretory signal of yeast α mating factor.

13. The culture of claim 8, wherein the expression vector is pPIC9 modified to contain a nucleotide sequence encoding PDGF.

14. The method according to claim 1, wherein said mutant is altered at the Arg159, Lys160 and Lys161 residues with an anionic or polar, uncharged amino acid.

15. The culture according to claim 8, wherein said mutant is altered at the Arg159, Lys160 and Lys161 residues with an anionic or polar, uncharged amino acid.

16. The method according to claim 14, wherein said amino acid is glutamic acid or serine.

17. The method according to claim 16, wherein said mutant comprises the sequence Glu159, Glu160, Glu161;

Ser159, Ser160, Ser161; or

Ser159, Lys160, Lys161.

18. The culture according to claim 15, wherein said amino acid is glutamic acid or serine.

19. The culture according to claim 18, wherein said mutant comprises the sequence Glu159, Glu160, Glu161;

Ser159, Ser160, Ser161; or

Ser159, Lys160, Lys161.

* * * * *